(12) United States Patent
Groteke et al.

(10) Patent No.: US 7,546,651 B2
(45) Date of Patent: Jun. 16, 2009

(54) HEAD AND UPPER NECK SUPPORT DEVICE

(75) Inventors: Eric K. Groteke, Safety Harbor, FL (US); Harry Chororos, Sarasota, FL (US); Walter M. Groteke, Safety Harbor, FL (US)

(73) Assignee: Back2Sleep LLC, Safety Harbor, FL (US)

( * ) Notice: Subject to any disclaimer, the term of this patent is extended or adjusted under 35 U.S.C. 154(b) by 0 days.

(21) Appl. No.: 12/004,900

(22) Filed: Dec. 21, 2007

(65) Prior Publication Data
US 2008/0163428 A1    Jul. 10, 2008

(51) Int. Cl.
*A47G 9/00* (2006.01)
(52) U.S. Cl. .......................................... 5/636
(58) Field of Classification Search ..................... 5/636, 5/638, 640, 632
See application file for complete search history.

(56) References Cited

U.S. PATENT DOCUMENTS

| | | | |
|---|---|---|---|
| 4,850,067 A | 7/1989 | Latorre | |
| 4,918,774 A | 4/1990 | Popitz | |
| 5,014,377 A | 5/1991 | Dixon | |
| 5,123,132 A | 6/1992 | Dixon | |
| 5,457,832 A | 10/1995 | Tatum | |
| 6,574,809 B1* | 6/2003 | Rathbun | 5/636 |
| 6,671,906 B1* | 1/2004 | Milligan | 5/636 |
| 6,671,907 B1 | 1/2004 | Zuberi | |
| 6,751,818 B2 | 6/2004 | Troop | |
| 6,817,049 B1 | 11/2004 | Hall | |
| 6,981,288 B1* | 1/2006 | Hu | 5/636 |
| 7,077,141 B2 | 7/2006 | Troop | |
| 7,082,633 B1* | 8/2006 | Maarbjerg | 5/636 |
| 7,100,227 B2 | 9/2006 | Frisbee | |
| 7,213,280 B2 | 5/2007 | Lavin et al. | |

* cited by examiner

*Primary Examiner*—Alexander Grosz
(74) *Attorney, Agent, or Firm*—Laurence A. Greenberg; Werner H. Stemer; Ralph E. Locher

(57) ABSTRACT

The invention is a head and neck support apparatus comprised of a central portion with three primary sections 1) a shoulder ramp, 2) an inclined Atlanto-Axial support (AXS) section, and 3) a substantially level head support section. The apparatus also has side support portions, in several embodiments, so a user may lay in a lateral position. The AXS section is designed to support the soft tissue between the user's atlanto and axis at 0 to 20 degrees.

15 Claims, 5 Drawing Sheets

HEAD AND UPPER NECK SUPPORT DEVICE

BACKGROUND OF THE INVENTION

1. Field of the Invention

This invention relates to head and neck support apparatuses, in particular support apparatuses to help maintain a reclining human in a healthful position to reduce sleep apnea and other sleep disorders.

2. Brief Description

This invention relates to an apparatus suitable for the prevention and/or reduction of sleep apnea. More particularly, this invention relates to a pillow which optimizes the user's breathing passageways by proper head, neck and shoulder positioning.

Sleep apnea is characterized by partial or complete occlusion of the upper airway passage during sleep while snoring is an indication of a partial occlusion of the upper airway. Obstructive sleep apnea sufferers repeatedly choke on their tongue and soft palate throughout an entire sleep period resulting in lowered arterial blood oxygen levels and poor quality of sleep. It should be realized that although the following specification discusses sleep apnea in detail, the present invention also applies to the treatment of other forms sleep disorders.

It has been found that the application of continuous positive airway pressure (CPAP) provides what can be described as a "pneumatic splint", supporting and stabilizing the upper airway and thus eliminating the occurrence of upper airway occlusions. It is effective in eliminating both snoring and obstructive sleep apnea and in many cases, can be effective in treating central and mixed apneas.

The long term effects of CPAP therapy are unknown so it is desirable to find other less intense or invasive treatments. It has been found that CPAP induces patients to swallow and this inducement to swallow can be reduced by lowering the airway pressure or removing the CPAP treatment completely. In addition to the problems associated with administering CPAP therapy there exists the inconvenience and cost of diagnosis which is currently undertaken by overnight observation at a sleep clinic or the like.

Snoring is an indication that the breathing passageways of an individual are partially blocked and thus is suffering from obstructive sleep apnea. The partial blockage of the breathing passageways during snoring means less oxygen is reaching the blood system and thus there is a greater chance that the individual will be subject to health problems such as heart attacks, strokes and hypertension, all of which are related to the amount of oxygen in the blood stream. Sleep apnea, a disorder where a victim stops breathing hundreds of times a night, represents even a more severe health hazard which can lead to the above health problems as well as daytime drowsiness and even narcolepsy in the more severe cases.

The causes for snoring include, among other, tongue obstruction (hypopharynx); nasal obstruction (colds, broken nose, etc.); excessive soft palate tissue; pharyngeal narrowing or elasticity; the presence of enlarged tonsils and/or adenoids; and sleep posture.

As the problems associated with snoring and sleep apnea are so acute, various articles have been placed on the market in an attempt to provide solutions. These articles have proven to both vary in price, comfort and effectiveness. For instance, articles placed on the market to confront the problems associated with snoring include: (1) indicators which indicate when the sleeper has moved to his back—a position that leads to increased snoring; (2) tongue retaining devices; (3) elastic masks and splints to keep the mouth open; (4) various drugs which stimulate those portions of the body inductive to snoring; (5) expensive forced air machines; and (6) modified pillow shapes.

The foregoing articles known in the prior art have not proven entirely satisfactory to those suffering from sleep disorders. The inadequacies of the prior art result from, among other things, in their being either too expensive, too uncomfortable, ineffective or any combination of the same.

OBJECTS OF THE INVENTION

An object of the present invention is to provide a pillow which, inter alia, solves or at least reduces the aforementioned problems. That is, an object of the present invention is to provide an anti-sleep apnea pillow which is effective in reducing or preventing sleep apnea, and which is comfortable, yet inexpensive to manufacture.

In achieving such objectives, the present invention utilizes a novel design which provides for optimal breathing passageways for the user while sleeping. The optimal breathing passageways are achieved by proper positioning of the user's head, neck and shoulders. Furthermore, optimization of the breathing passageways is achieved without reducing the comfort level of the user. Rather, the present invention provides a high degree of comfort for both back and side sleepers.

The amount of reduction in snoring depends, to a large extent, on which of the aforementioned factors are causing the sleep apneas. It is clear, though, that by proper positioning of the head and the maintaining of optimal breathing passageways, many of the factors leading to sleep apnea can be reduced if not eliminated entirely.

Generally, those who are problem snorers and thus most likely suffer from obstructive sleep apnea, are those who sleep on their back or on their side, with those sleeping on their back usually being somewhat noisier than those sleeping on their side. This observation is illustrative of the fact that the position of a person's breathing passageways is an important factor in whether and to what degree a person will snore. Therefore, sleep posture can be said to play a role in either aggravating or lessening the severity of sleep apnea and snoring. The present invention is directed at providing a comfortable pillow and a pillow which will ensure optimal breathing passageways so as to reduce sleep apnea for both those who sleep on their back and those who sleep on their side.

Basically, obstructive sleep apnea and snoring can occur due to a partial obstruction at each or a combination of the following:

(1) Nasal—This is often due to nasal obstruction from polyps, a deviated septum, allergies or a common cold. These causes, for the most part, are only correctable by surgery or, as in the case of a cold, are temporary.

(2) Nasopharynx—Individuals having relatively large amounts of soft tissue (or more easily extendable soft tissue) at the back of their mouth where the "soft palate" or uvula meets the back of the throat (the area referred to as the nasopharynx) are likely to have obstructive breathing problems. This area, comprising the uvula and soft palate and pharyngeal folds, vibrates or flutters during breathing and can cause a sound loud enough to even awaken a sound sleeper.

(3) Hypopharynx—This third area of the airway is the area at the back of the mouth where the tongue meets the pharynx. In order to keep the tongue from falling backward and blocking the airway, it is helpful to thrust the jaw forward. Since the tongue is connected to the jaw, the thrusting forward of the jaw tends to keep the relaxed tongue from partially or completely blocking the back of the throat.

In addition, it has been determined that the position of one's jaw with respect to one's clavicle has an effect on the clearness of one's breathing passageways. When the jaw is placed close to one's chest or clavicle area, the breathing passageways become less clear. This position of the jaw leads to narrowing or constriction of the airway and an increase in snoring. Additionally, when the jaw is moved too far from ones chest (i.e., head tilted back to a great extent), the breathing passageways become less clear. This positioning of the head induces the hypopharynx to move to a partially blocked position and increases the chances of the relaxed tongue curling back and creating blockage. A position of the head between these extremes has been found to lead to an optimization of a person's breathing passageways. More specifically the head should be positioned such that the neck is pushed outwardly and the head curled back a bit such that the bottom surface of the chin lies virtually in the same plane as the upper surface of the neck.

Moreover, a twisting of the head while the rest of the body remains stationary tends to create a narrowing or a reduction in the area of the breathing passageways. Thus a person lying on his back with his head twisted to one side will not have as clear passageways as one having his head untwisted. Also, a person lying on his side would have partially blocked breathing passageways when the head is twisted down towards the sleeping surface.

Accordingly, it can be seen that the position of a person's head while sleeping plays an important role in how clear the person's breathing passageways are. Furthermore, as there is a correlation between the clearness of one's breathing passageways and the presence of sleep apnea, sleep posture can tend to aggravate or lessen the severity of sleep apnea.

Another object of some embodiments of the present invention is to also provide elevation of the shoulders and in some embodiments the torso as well, to prevent or mitigate the occurrence of acid reflux in the esophagus. It has been shown that elevating a person's head, shoulders, and torso can decrease the occurrence of acid reflux in the esophagus. Typically, a person's head needs to be raised by more than 2 inches before relief is experienced.

Yet another object of many embodiments of the present invention is to position a person in a healthful position to facilitate proper blood circulation. Still another object of many embodiments of the present invention is to provide traction or decompression of the spine. Whereas the AXS and wedge serve to better align the vertebral bodies of the cervical spine and improve the cervical lordosis.

SUMMARY OF THE INVENTION

The invention, a head and neck support apparatus, is comprised of a central portion with three primary sections 1) a shoulder ramp, 2) an inclined Atlanto-Axial support (AXS) section, and 3) a substantially level head support section. The apparatus also has side support portions, in several embodiments, so a user may lay in a lateral position. The AXS section is designed to support the soft tissue between the user's atlanto and axis at 0 to 20 degrees. In several embodiments the angle is fixed at 16 degrees, which has been found to give very good results for most individuals. In another embodiment the angle of the AXS section can be adjusted between 0 to 20 degrees. The invention is preferably constructed with a multi-density foam core with multi-density viscoelastic material covering the foam core.

The invention, a head and neck support apparatus, could be used as a pillow; a headrest of a chair; a headrest of a bed; or any application where such an apparatus may be advantageous. The invention as described in this disclosure pertains to use on primates and more particularly humans. The invention could be constructed of any suitable material known in the art, but preferably is constructed of a combination of resilient and visco-elastic material. Various types of foams are ideal, due to manufacturability, but other materials could be used.

In one embodiment the invention is an apparatus for supporting and positioning a head and a neck of a primate to relieve or mitigate a sleeping disorder comprising: a supportive core constructed of resilient material, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position.

In another embodiment the invention is an apparatus for supporting and positioning a head and a neck of a primate to relieve or mitigate a sleeping disorder comprising a supportive core constructed of resilient material, with said supportive core comprising, a core AXS portion with an inclined AXS constructed of more resilient material than the other portions of the supportive core, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position.

In yet another embodiment the invention is an apparatus for supporting and positioning a head and a neck of a primate to relieve or mitigate a sleeping disorder comprising a supportive core constructed of resilient material of which comprises portions made of at least two different densities of foam, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position.

In still another embodiment the invention is an apparatus for supporting and positioning a head and a neck of a primate to relieve or mitigate a sleeping disorder comprising: a supportive core constructed of resilient material, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 16 and 20 degrees while said primate is in a substantially supine position.

In yet still another embodiment the invention is an apparatus for supporting and positioning a head and a neck of a primate to relieve or mitigate a sleeping disorder comprising: a supportive core constructed of resilient material, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint at approximately 16 degrees while said primate is in a substantially supine position.

In but another embodiment the invention is an apparatus for supporting and positioning a head and a neck of a primate to relieve or mitigate a sleeping disorder comprising a supportive core constructed of resilient material of which comprises portions made of at least two different densities of foam, with said supportive core comprising, a core AXS portion, which is the densest portion of the core, with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position.

In but still another embodiment the invention is an apparatus for supporting and positioning a head and a neck of a primate to relieve or mitigate a sleeping disorder comprising: a supportive core constructed of resilient material, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position and the primate's head is elevated at least 3 inches above the base of the apparatus.

In yet but still another embodiment the invention is an apparatus for supporting and positioning a head and a neck of a primate to relieve or mitigate a sleeping disorder comprising: a supportive core constructed of resilient material, with said supportive core comprising, a core AXS portion with an inclined AXS, a shoulder ramp portion for elevating said primates shoulders, and at least two side head support portions; an upper support layer constructed of visco-elastic material placed on top of said supportive core, with said upper support layer comprising a upper head support portion, at least two upper side head support portions that are elevated above said upper head support portion, an upper shoulder ramp portion, and at least two upper side shoulder ramp portions; wherein said AXS portion positions the primate's Atlanto-Axial joint between 0 and 20 degrees while said primate is in a substantially supine position and wherein said upper support layer is constructed with portions of at least two different densities of visco-elastic material.

In yet still another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position.

In still another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said supportive core is constructed of portions made of at least two different densities of foam.

In but still another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said upper support layer is constructed of portions made of at least two different densities of visco-elastic foam.

In still but another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said supportive core is constructed of portions made of at least two different densities of foam, and said upper support layer is constructed of portions made of at least two different densities of visco-elastic foam.

In yet still another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and the primate's head is elevated at least 3 inches above the base of the apparatus.

In still yet another embodiment the invention is an apparatus for supporting and positioning a head and a neck of a primate to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of visco-elastic material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint at approximately 16 degrees while said primate is in a substantially supine position.

In yet another embodiment the invention is an apparatus for supporting and positioning a head and a neck of a human to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of flexible soft material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position.

In still yet but another embodiment the invention is an apparatus for supporting and positioning a head and a neck of a human to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of flexible soft material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said supportive core is constructed of portions made of at least two different densities of foam.

In but another embodiment the invention is an apparatus for supporting and positioning a head and a neck of a human to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of flexible soft material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said upper support layer is constructed of portions made of at least two different densities of foam.

In yet another embodiment the invention is an apparatus for supporting and positioning a head and a neck of a human to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of flexible soft material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and said supportive core is constructed of portions made of at least two different densities of foam, and said upper support layer is constructed of portions made of at least two different densities of foam.

In still another embodiment the invention is an apparatus for supporting and positioning a head and a neck of a human to relieve or mitigate sleep apnea comprising: a supportive core constructed of resilient material, with said supportive core comprising: a core AXS portion with an inclined AXS, a shoulder ramp portion for elevating said primates shoulders, and at least two elevated side head support portions; an upper support layer constructed of flexible soft material affixed on top of said supportive core, with said upper support layer comprising: an upper head support portion, an upper AXS portion with an inclined AXS constructed to compliment said core AXS portion, at least two upper side head support portions that are elevated above said upper head support portion, an upper shoulder ramp portion, and at least two upper side shoulder ramp portions; wherein said AXS portions position the primate's Atlanto-Axial joint between 0 and 20 degrees while said primate is in a substantially supine position and the primate's head is elevated at least 3 inches above the base of the apparatus.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DETAILED DESCRIPTION

Figure 1:
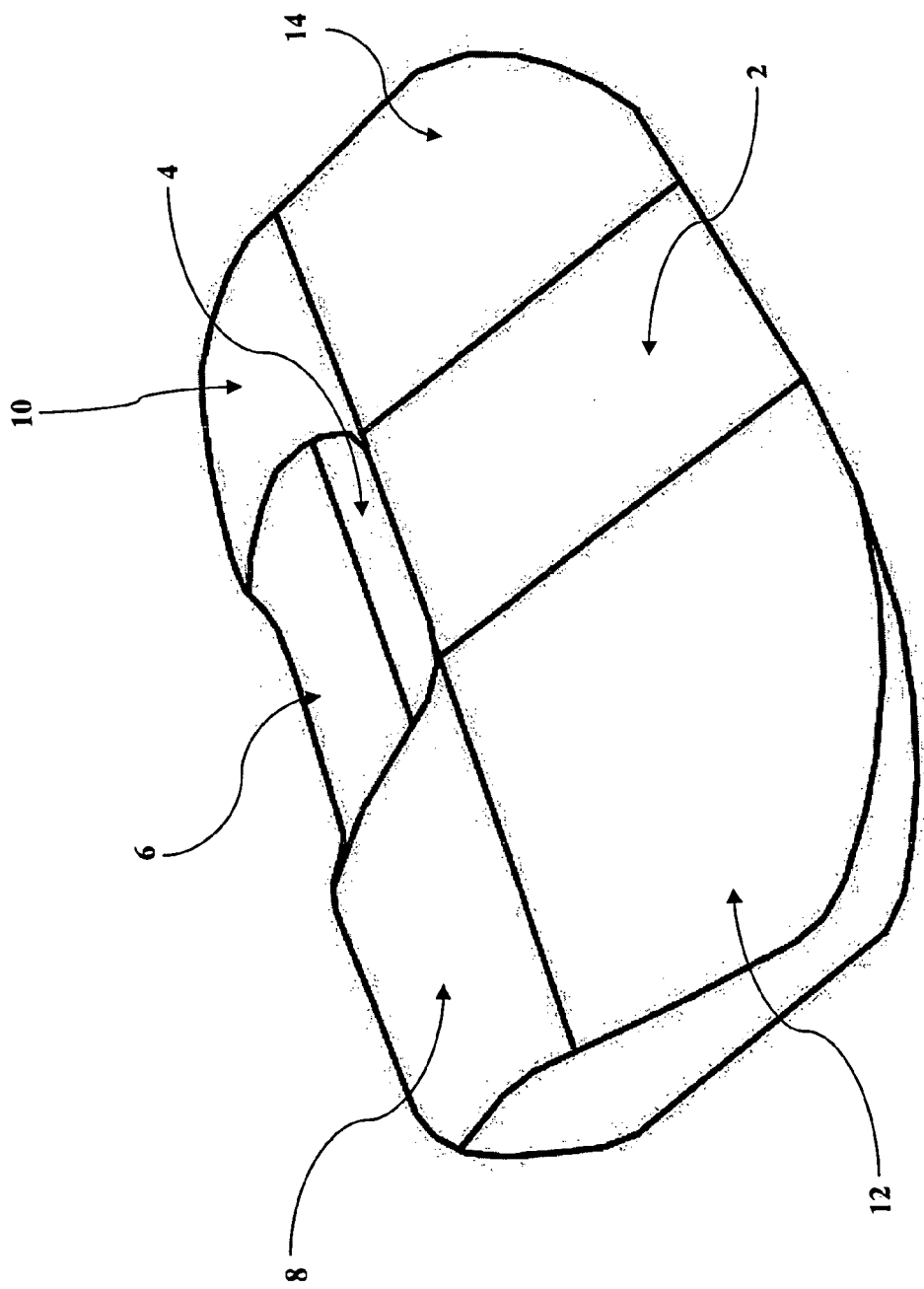
FIG. 1 shows an axonometric view of an apparatus embodying the invention.

FIG. 1 shows an axonometric view of an apparatus embodying the invention comprising a central portion with three sections, a shoulder ramp 2, an inclined Atlanto-Axial support (AXS) section 4, and a substantially level head support section 6. The apparatus also comprises side head supports 8 and 10; and side shoulder ramps 12 and 14. Preferably the AXS section 4 is constructed of the hardest and most resilient material used in the present apparatus, though the section could be covered with a relatively thin layer of visco-elastic material such as visco-elastic polyurethane foam. Though the AXS section 4 could simply be constructed of a highly resilient polyurethane foam alone. The AXS section 4 should be relatively stiff and hard to ensure the proper positioning of the neck and more specifically the Atlanto-Axial joint.

Preferably the raised side head supports 8 and 10, are constructed so as to provide the second most resilient and the second hardest level of support after the AXS section 4 of the apparatus. The side head supports 8 and 10 are used in the supine position to keep the users head from turning to one side or the other, as twisting of the head can constrict the users airways. The side head supports 8 and 10 are also intended to work with the softer side shoulder ramps 12 and 14 to position the users head, neck, and shoulders in a healthful way while in the lateral position. The side head supports give relatively firm support to keep the head and spine aligned in the lateral position. While the softer side shoulder ramps 12 and 14 allow the users shoulders to "sink into" the apparatus, so the users spine is positioned substantially straight. Preferably the side shoulder ramps 12 and 14 are the softest and least resilient sections of the apparatus.

Preferably the central shoulder ramp 2 is constructed to provide relatively soft support, but enough to elevate the user's shoulders. The level head support section 6 should also be constructed to provide relatively soft support. The head support section 6 needs to only be firm enough to support the users head in a healthful position, otherwise the considerations for level of support targeted toward comfort.

Figure 2:
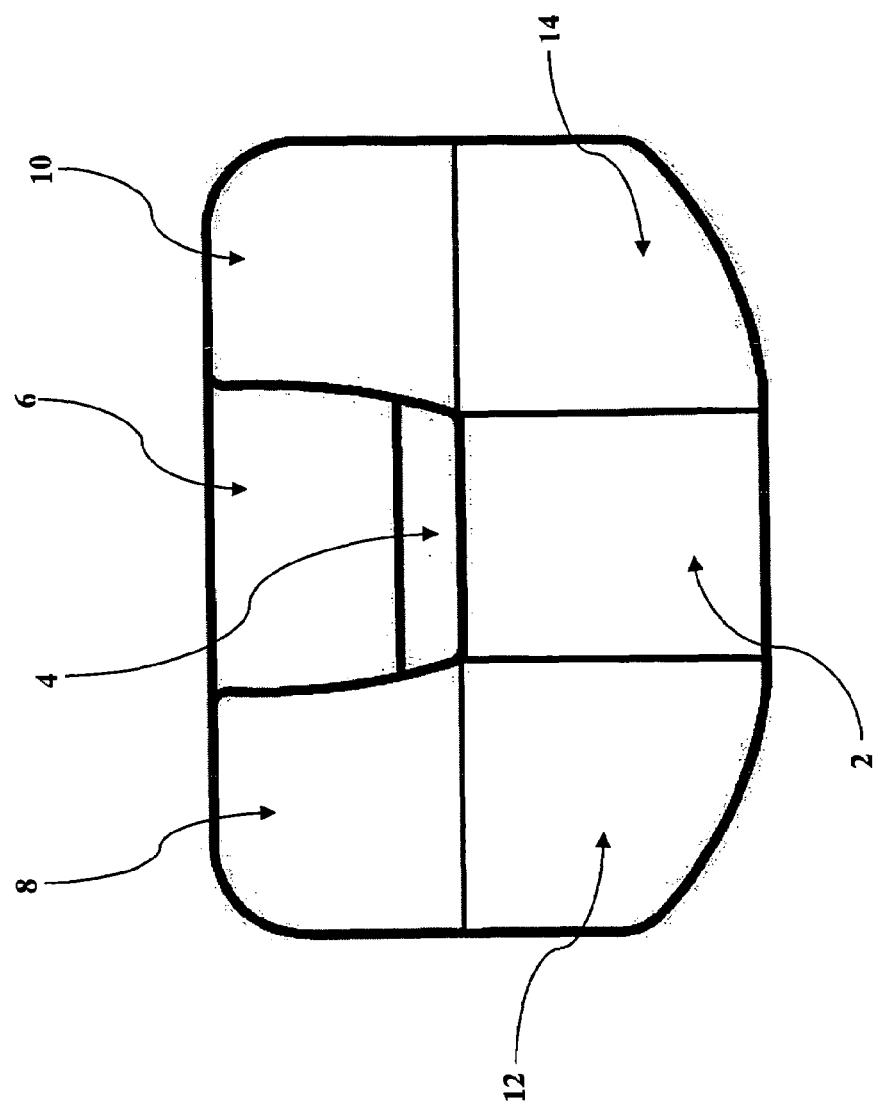
FIG. 2 shows an overhead, plan, view of an apparatus embodying the invention.

FIG. 2 shows an overhead, plan, view of an apparatus embodying the invention comprising a central portion with three sections, a shoulder ramp 2, an inclined AXS section 4, and a substantially level head support section 6. The apparatus also comprises side head supports 8 and 10; and side shoulder ramps 12 and 14.

Figure 3:
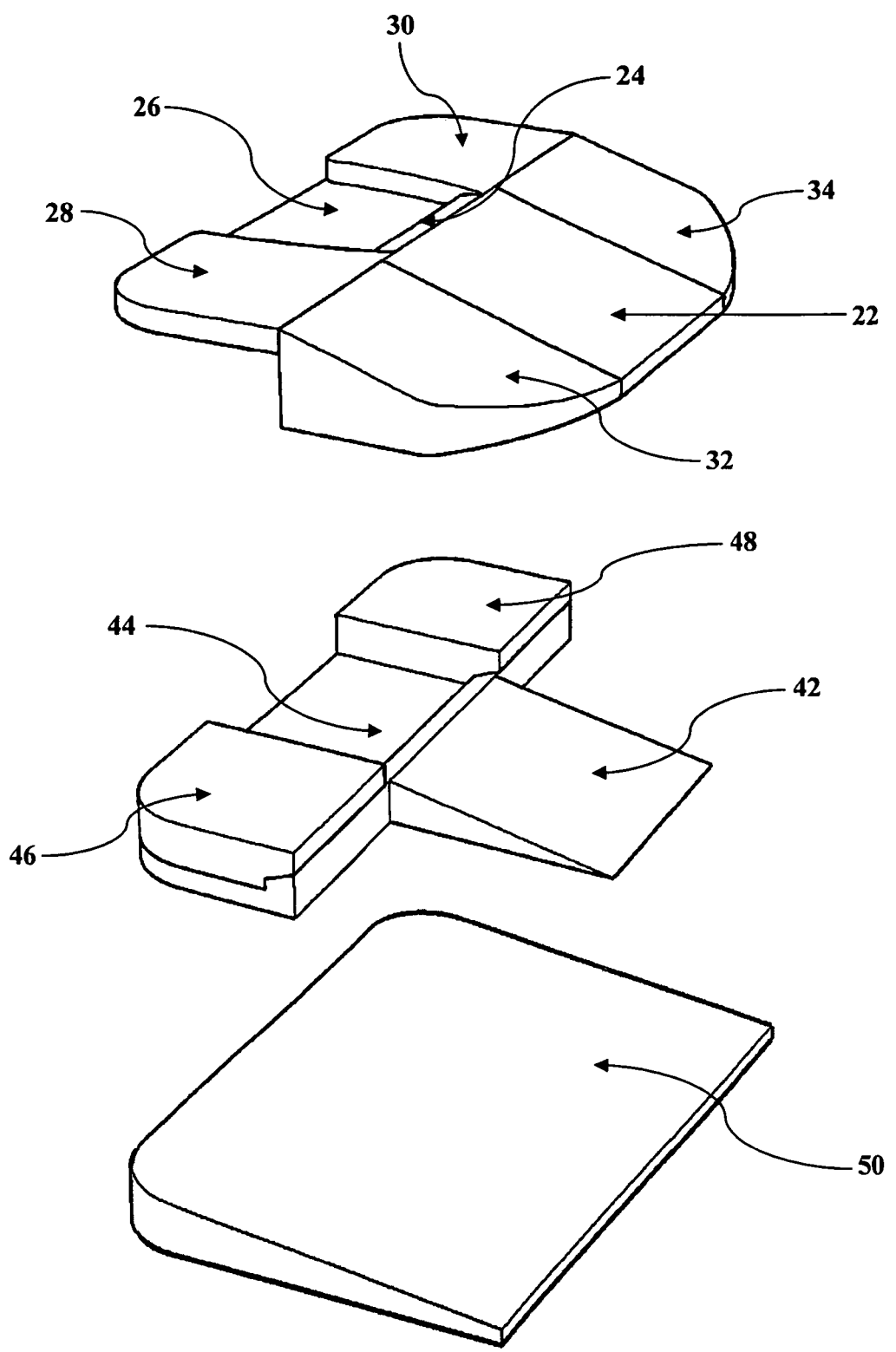
FIG. 3 shows a partially exploded view of an apparatus embodying the invention.

FIG. 3 shows a partially exploded view of a particular embodiment of the invention. The portions grouped in the upper most part of FIG. 3 are preferably constructed of visco-elastic materials, although none visco-elastic materials could be used, but without some of the advantages of the preferred embodiments. The portions grouped in the upper most part of FIG. 3 and preferably made of visco-elastic materials include upper shoulder ramp portion 22, upper AXS portion 24, upper head support portion 26, upper side head support portions 28 and 30, and upper side shoulder ramp portions 32 and 34.

The portions grouped in the middle part of FIG. 3 are preferably constructed of resilient materials, most preferably a resilient foam. The portions grouped in the upper part of FIG. 3 and preferably made of resilient materials include core shoulder ramp portion 42, core AXS portion 44, and core side head support portions 46 and 48. The purpose of these core portions is to provide structural support for the apparatus and therefore to provide support to the user.

The portion at the bottom of FIG. 3 is elevation wedge 50, which can optionally be used to put the user in more of a reclined position and to further elevate the user. It is envisioned that the wedge could be made of varying heights and angles, to customized the apparatus to a user desired position while still receiving the benefit of the AXS section.

Figure 4:
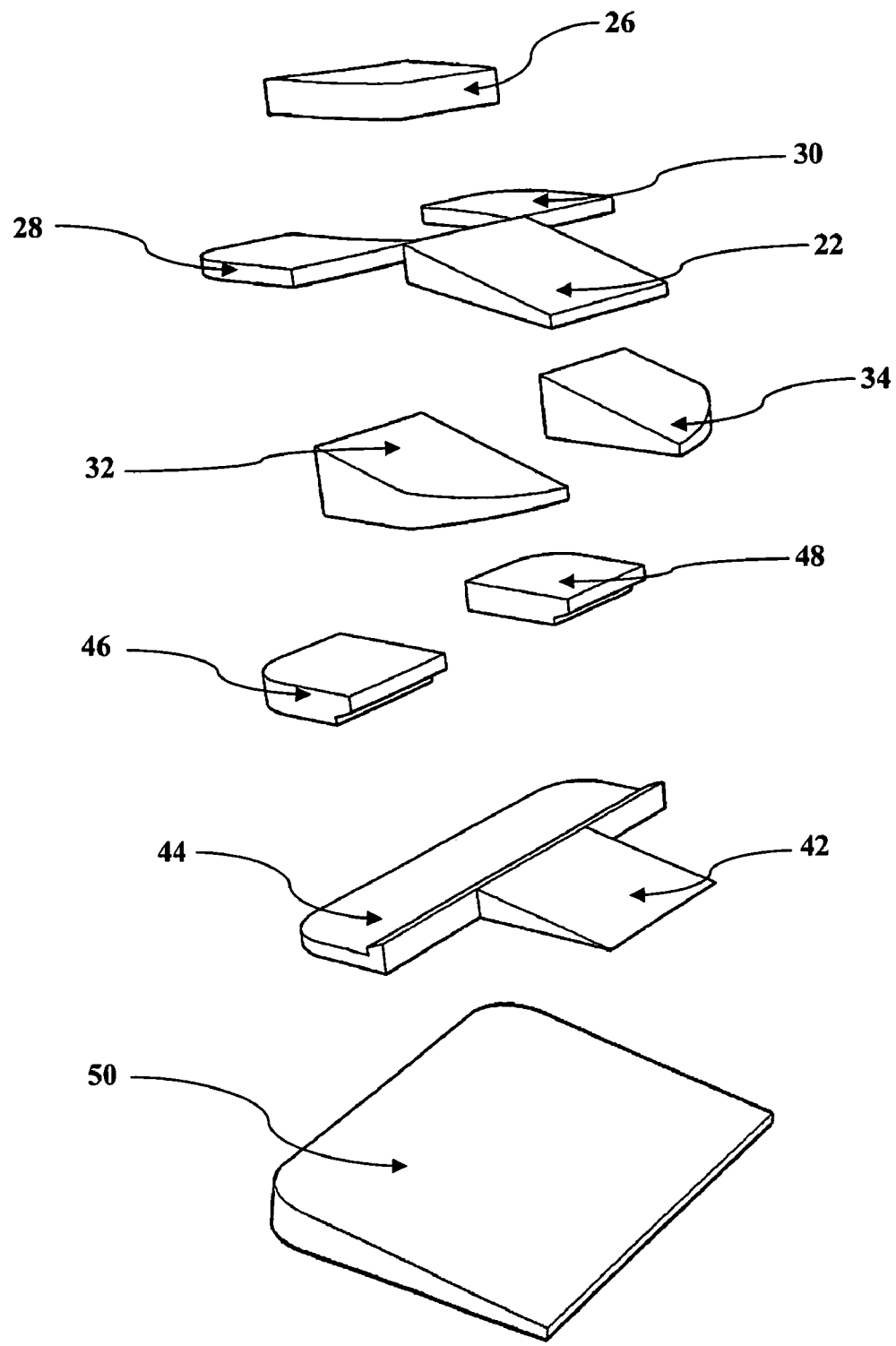
FIG. 4 shows an exploded view of an apparatus embodying the invention.

FIG. 4 shows an exploded view of an apparatus embodying the invention. FIG. 4 shows the similar portions as shown in FIG. 3 except in a fully exploded view to further illustrate how this preferred embodiment is assembled and without the upper AXS portion. The AXS section 4 (shown in FIG. 1 and FIG. 2) is simply comprised of the core AXS portion 44. As should be apparent the various portions can be made of materials of varying properties to obtain the effect desired. The various portions can be assembled and connected by any method known in the art, including but not limited to gluing; using tack fasteners; using auger anchors; heat sealing the portions together; using a formed casing to keep the portions together and properly positioned, using a polymer coating to keep the portions together; or any combination of the above or other methods known in the art. Elevation wedge 50 may be assembled into the apparatus or may be separate from the apparatus so that a user could simply place the wedge under the apparatus to change the incline and elevation of the apparatus. The wedge could also have some way of keeping the wedge temporally in place, such as hook-and-loop fasteners, snap bottoms, or some other fastening device to keep the wedge and apparatus properly aligned.

Figure 5:
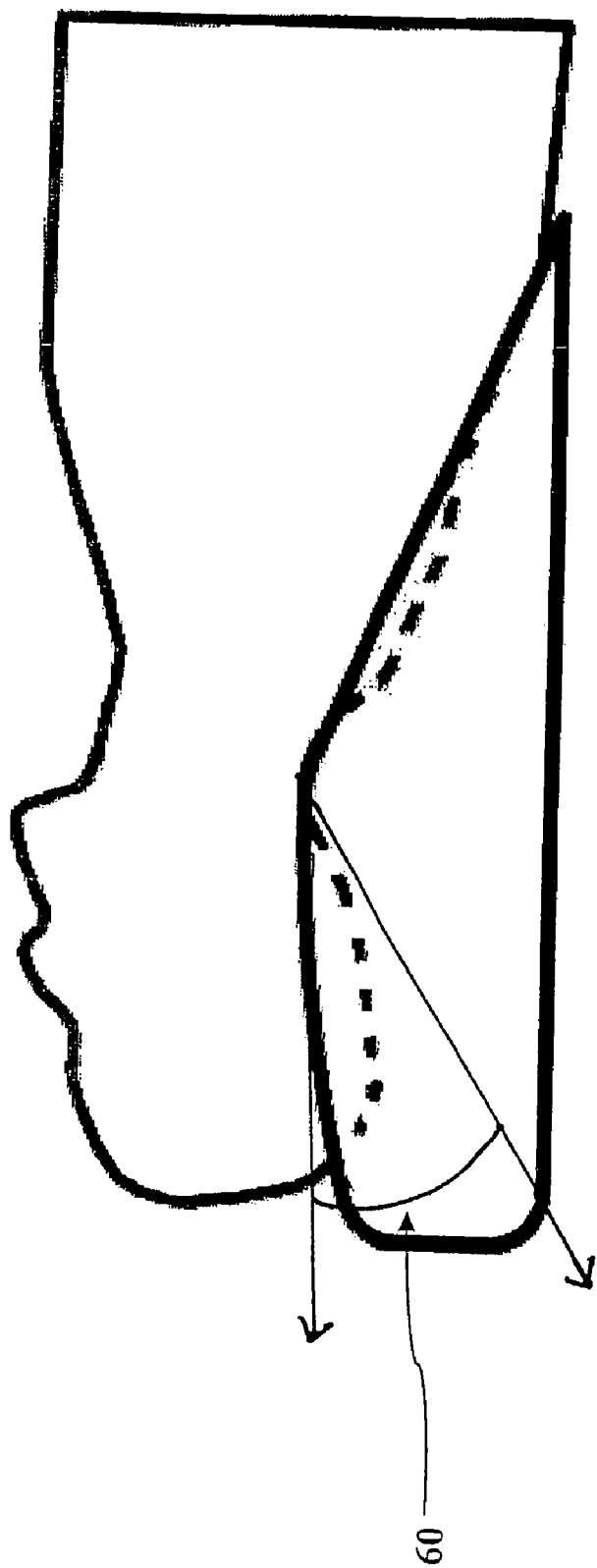
FIG. 5 shows a side elevation view of a person, in a supine position, using an apparatus embodying the invention.

FIG. 5 shows a side elevation view of a person, in a supine position, using an apparatus embodying the invention. FIG. 5 shows the AXS angle 60 that can be critical to the effectiveness of the apparatus. As mentioned above 16 degrees of downward inclination has been shown to give optimal results for most persons, though any angle from 0 to 20 degrees may be effective for any given user depending on their specific physiology or pathology.

The actual dimensions of the apparatus will depend on the size and dimensions of the user, as well as their particular physiology or pathology. It is envisioned with the advancements in the field of foam construction and rapid prototyping that embodiments of the present invention could be custom made to each user. This could be accomplished by taking measurements of the particular user's dimensions and estimating the weight of said user's to construct a perfectly matched support apparatus. Alternatively the apparatus could be constructed of varying sizes and foam densities to roughly accommodate most potential users, much the way running shoes are made in different sizes with different levels of cushioning. This would allow a potential user to try several differently constructed embodiments of the present invention to see which one fits the user's requirements best.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. An apparatus for supporting and positioning a head and a neck of a primate to relieve or mitigate a sleeping disorder comprising:
    a supportive core constructed of resilient material, with said supportive core comprising:
    a core AXS portion with an inclined AXS support,
    a shoulder ramp portion for elevating said primate's shoulders, and
    at least two side head support portions;
    an upper support layer constructed of visco-elastic material placed on top of said supportive core, with said upper support layer comprising:
    an upper head support portion,
    at least two upper side head support portions that are elevated above said upper head support portion,
    an upper shoulder ramp portion, and
    at least two upper side shoulder ramp portions;
    wherein said core AXS portion positions the primate's Atlanto-Axial joint at approximately 16-20 degrees while said primate is in a substantially supine position, and the primate's head is elevated at least 3 inches above the base of the apparatus.

2. The apparatus of claim 1 wherein said AXS portion of said supportive core is constructed of more resilient material than the other portions of the supportive core.

3. The apparatus of claim 1 wherein said supportive core comprises portions made of at least two different densities of foam.

4. The apparatus of claim 3 wherein said AXS portion is constructed of denser foam than the other portions of the supportive core.

5. The apparatus of claim 1 wherein said supportive core comprises portions made of at least two densities of polyurethane foam.

6. The apparatus of claim 1 wherein said AXS portion positions the primate's Atlanto-Axial joint at approximately 16 degrees.

7. The apparatus of claim 1 wherein said upper support layer is constructed with portions of at least two different densities of visco-elastic material.

8. An apparatus for supporting and positioning a head and a neck of a primate to relieve or mitigate sleep apnea comprising:
    a supportive core constructed of resilient material, with said supportive core comprising:
    a core AXS portion with an inclined AXS support,
    a shoulder ramp portion for elevating said primate's shoulders, and
    at least two elevated side head support portions;
    an upper support layer constructed of visco-elastic material affixed on top of said supportive core, with said upper support layer comprising:
    an upper head support portion,
    an upper AXS portion with an inclined AXS constructed to compliment said core AXS portion,
    at least two upper side head support portions that are elevated above said upper head support portion,
    an upper shoulder ramp portion, and
    at least two upper side shoulder ramp portions;
    wherein said AXS portions position the primate's Atlanto-Axial joint between at approximately 16-20 while said primate is in a substantially supine position and the primate's head is elevated at least 3 inches above the base of the apparatus.

9. The apparatus of claim 8 wherein said supportive core is constructed of portions made of at least two different densities of foam.

10. The apparatus of claim 8 wherein said upper support layer is constructed of portions made of at least two different densities of visco-elastic foam.

11. The apparatus of claim 8 wherein said supportive core is constructed of portions made of at least two different densities of foam, and said upper support layer is constructed of portions made of at least two different densities of visco-elastic foam.

12. An apparatus for supporting and positioning a head and a neck of a human to relieve or mitigate sleep apnea comprising:
    a supportive core constructed of resilient material, with said supportive core comprising:
    a core AXS portion with an inclined AXS support,
    a shoulder ramp portion for elevating said primate's shoulders, and
    at least two elevated side head support portions;
    an upper support layer constructed of flexible soft material affixed on top of said supportive core, with said upper support layer comprising:
    an upper head support portion,
    an upper AXS portion with an inclined AXS constructed to compliment said core AXS portion,
    at least two upper side head support portions that are elevated above said upper head support portion, an upper shoulder ramp portion, and at least two upper side shoulder ramp portions;

wherein said AXS portions position the primate's Atlanto-Axial joint between at approximately 16-20 while said primate is in a substantially supine position and the primate's head is elevated at least 3 inches above the base of the apparatus.

13. The apparatus of claim 12 wherein said supportive core is constructed of portions made of at least two different densities of foam.

14. The apparatus of claim 12 wherein said upper support layer is constructed of portions made of at least two different densities of foam.

15. The apparatus of claim 12 wherein said supportive core is constructed of portions made of at least two different densities of foam, and said upper support layer is constructed of portions made of at least two different densities of foam.

* * * * *